(12) United States Patent
Sun et al.

(10) Patent No.: US 12,280,270 B2
(45) Date of Patent: Apr. 22, 2025

(54) LED THERAPEUTIC DEVICE

(71) Applicant: Oral IQ LLC, Los Angeles, CA (US)

(72) Inventors: Grace Sun, Los Angeles, CA (US); Hans Kristian Skjorshammer, Los Angeles, CA (US)

(*) Notice: Subject to any disclaimer, the term of this patent is extended or adjusted under 35 U.S.C. 154(b) by 117 days.

(21) Appl. No.: 17/485,224

(22) Filed: Sep. 24, 2021

(65) Prior Publication Data

US 2023/0099922 A1  Mar. 30, 2023

(51) Int. Cl.
*A61N 5/06* (2006.01)

(52) U.S. Cl.
CPC .... *A61N 5/0613* (2013.01); *A61N 2005/0651* (2013.01); *A61N 2005/0659* (2013.01); *A61N 2005/0662* (2013.01)

(58) Field of Classification Search
CPC ......... A61N 5/0613; A61N 2005/0651; A61N 2005/0659; A61N 2005/0662; A61N 2005/0606; A61N 2005/0607; A61N 2005/0626; A61N 2005/0644; A61N 2005/0665
See application file for complete search history.

(56) References Cited

U.S. PATENT DOCUMENTS

| | | | | |
|---|---|---|---|---|
| 2002/0046938 A1* | 4/2002 | Donofrio | ................ | H01H 9/04 200/302.1 |
| 2008/0051856 A1* | 2/2008 | Vizethum | .............. | A61N 5/062 607/80 |
| 2008/0208297 A1* | 8/2008 | Gertner | ................ | A61N 5/0603 607/92 |
| 2009/0088824 A1* | 4/2009 | Baird | ................... | A61N 5/0617 607/90 |
| 2009/0290608 A1* | 11/2009 | Kim | .................... | H01S 5/02212 372/36 |
| 2010/0179469 A1* | 7/2010 | Hammond | ........... | A61N 5/0624 604/20 |
| 2011/0313408 A1* | 12/2011 | Tankovich | ............ | H01S 3/0675 606/9 |
| 2012/0226268 A1* | 9/2012 | Liu | ...................... | A61N 5/0613 606/9 |
| 2014/0135798 A1* | 5/2014 | David | .................. | A61N 5/0624 606/131 |
| 2015/0310183 A1* | 10/2015 | Madhavan | ............. | G16H 40/67 705/2 |
| 2018/0169432 A1* | 6/2018 | Nishimura | .......... | A61M 5/1582 |

* cited by examiner

*Primary Examiner* — Gary Jackson
*Assistant Examiner* — Sebastian X Lukjan
(74) *Attorney, Agent, or Firm* — Tommy S F Wang; Wang IP Law Group, P.C.

(57) ABSTRACT

The present application discloses a LED therapeutic device comprising a top case, a light assembly, a controller, a switch assembly, a bottom case and a power supply. The light assembly comprises a lens and a LED assembly, wherein the lens is coupled to the top case and the LED assembly comprises at least one visible light LED and at least one infrared LED. The controller is coupled to the light assembly. The switch assembly is coupled to the controller. The bottom case is removably coupled to the top case. The power supply is electrically coupled to the controller.

12 Claims, 7 Drawing Sheets

| Basic Information | | | | | |
|---|---|---|---|---|---|
| Nominal Voltage | 3.6V | Rated Capacity | 2500mAh 9Wh | | |
| Charge Current | 1250mA | Maximum Continuous Charge Current | 2500mA | End Charge Current | 50mA |
| Cut-off Voltage | 2.75V | Maximum Discharge Current | 7500mA | Limited Charge Voltage | 4.2V |

FIG. 6A

| Test | | |
|---|---|---|
| Item | Sample* | Conclusion |
| Altitude Simulation | C1-C5, C6-C10 | Pass |
| Thermal Test | | Pass |
| Vibration | | Pass |
| Shock | | Pass |
| External Short Circuit | | Pass |
| Impact | C11-C15, C16-C20 | Pass |
| Forced Discharged | C21-C30, C31-C40 | Pass |

\* C1-C5: Cells at first cycle in fully charged states;
   C6-C10: Cells after 25 cycles ending in fully charged states;
   C11-C15: Cells at first cycle at 50% of the design rated capacity;
   C16-C20: Cells at 25 cycle at 50% of the design rated capacity;
   C21-C30: Cells at first cycle in fully discharged states;
   C31-C40: Cells after 25 cycles ending in fully discharged states.

FIG. 6B

LED THERAPEUTIC DEVICE

TECHNICAL FIELD OF THE INVENTION

The present application generally relates to medical devices, and more particularly, to a LED therapeutic device.

BACKGROUND OF THE INVENTION

Currently, people use red light or infrared light therapy units for temporary pain relief and promote physiotherapy efficiency such as muscular recovery and conditioning.

However, such therapy units are commonly heavily constructed, must consume alternated current (plug-in units), require specialty training, are costly and expensive. It is only suitable for clinic and facility usage and is not practical for the general public. Patient may not treat themselves on a daily basis. In addition, it may also cost a lot for frequent therapeutic visit.

Therefore, a need remains for a LED therapeutic device to provide a more convenient and therapeutic device for general public.

SUMMARY OF THE INVENTION

The present application discloses a LED therapeutic device to provide a more convenient and therapeutic device for general public.

The LED therapeutic device comprises a top case, a light assembly, a controller, a switch assembly, a bottom case and a power supply. The light assembly comprises a lens and a LED assembly wherein the lens is coupled to the top case and the LED assembly comprises at least one visible light LED and at least one infrared LED. The controller is coupled to the light assembly. The switch assembly is coupled to the controller. The bottom case is removably coupled to the top case. The power supply is electrically coupled to the controller.

According to an exemplary embodiment of the LED therapeutic device, wherein the LED assembly comprises two infrared LEDs. Wavelengths of the two infrared LEDs are 850 nm and 940 nm. A wavelength of the at least one visible light LED is 660 nm.

According to the other exemplary embodiment, wherein the LED assembly comprises two visible light LEDs. Wavelengths of the two visible light LEDs are 630 nm and 660 nm. A wavelength of the at least one infrared LED is 850 nm.

In various exemplary embodiments, wherein the light assembly further comprises a reflector and an insulator. The reflector is coupled between the lens and the LED assembly. The insulator is coupled between the reflector and the LED assembly.

In various exemplary embodiments, wherein top case comprises aluminum. More specifically, the top case is made of aluminum.

In various exemplary embodiments, wherein the bottom case comprises aluminum. More specifically, the bottom case is made of aluminum.

In various exemplary embodiments, wherein the controller comprises a circuit control block and a circuit control panel. The circuit control panel is surrounded by the circuit control block.

In various exemplary embodiments, wherein the switch assembly is located inside the top case.

In various exemplary embodiments, wherein the switch assembly comprises a switch board, a button, a switch retainer and a positioning retainer block. The switch board is coupled to the controller. The button is coupled to the switch board. The switch retainer is located between the button and the switch board. The switch board and the switch retainer are surrounded by the positioning retainer block.

In various exemplary embodiments, wherein the power supply comprises a positive anode board, an anode insulation pad, an o-ring, a battery spring, a battery and a battery barrel. The positive anode board is electrically coupled to the controller via the switch assembly. The anode insulation pad is coupled to the positive anode. The positive anode board and the anode insulation pad are surrounded by the o-ring. The battery is coupled between the battery spring and the positive anode board and is surrounded by the battery barrel.

In various exemplary embodiments, wherein the battery is a rechargeable battery.

In various exemplary embodiments, wherein the battery is a lithium battery.

Based on the above, the LED therapeutic device of the present application provide a portable device with lighter weight by utilize the aluminum as a main material for the top case and the bottom case. As such, patient may use the LED therapeutic device of the present application anywhere they want and on a daily basis.

In addition, the combination of visible light and infrared light may also provide a more therapeutic treatment for the patient. Specifically, compared with other wavelengths, it is evidence-based for the combined-usage of the wavelengths mentioned in the present application to have more clinical efficacy.

Numerous other advantages and features of the present application will become readily apparent from the following detailed description of disclosed embodiments, from the claims and from the accompanying drawings.

BRIEF DESCRIPTION OF THE DRAWINGS

The objects, features and advantages of the present application will be more readily appreciated upon reference to the following disclosure when considered in conjunction with the accompanying drawings, wherein like reference numerals are used to identify identical components in the various views, and wherein reference numerals with alphabetic characters are utilized to identify additional types, instantiations or variations of a selected component embodiment in the various views, in which:

FIGS. 6A-6B show general information and the test result of a battery of the LED therapeutic device.

DETAILED DESCRIPTION OF DISCLOSED EMBODIMENTS

Figure 1:
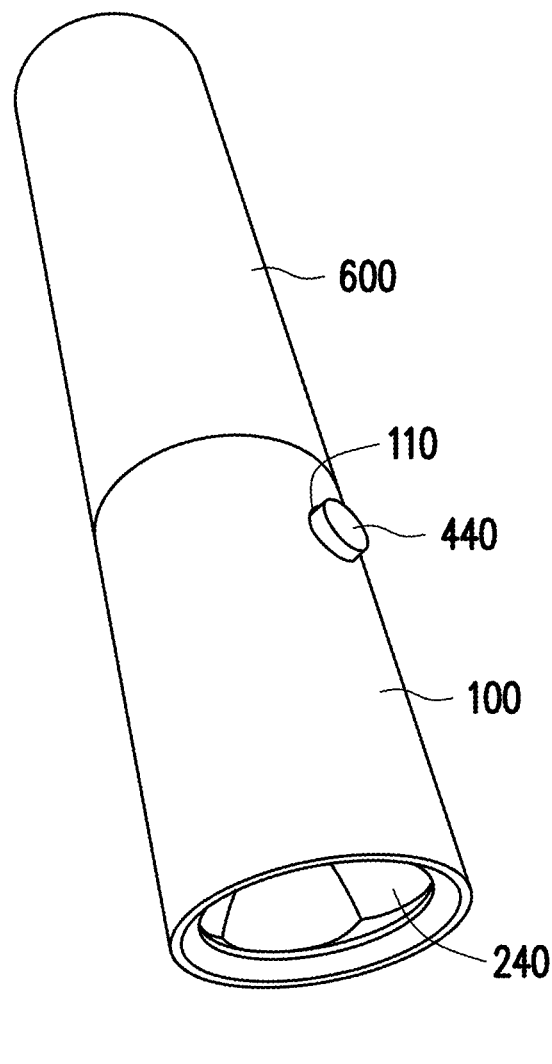
FIG. 1 is a perspective view of a LED therapeutic device.

Reference will now be made in detail to the present representative embodiments of the present application, examples of which are illustrated in the accompanying drawings. Wherever possible, the same reference numbers are used in the drawings and the description to refer to the same or like parts.

Figure 2:
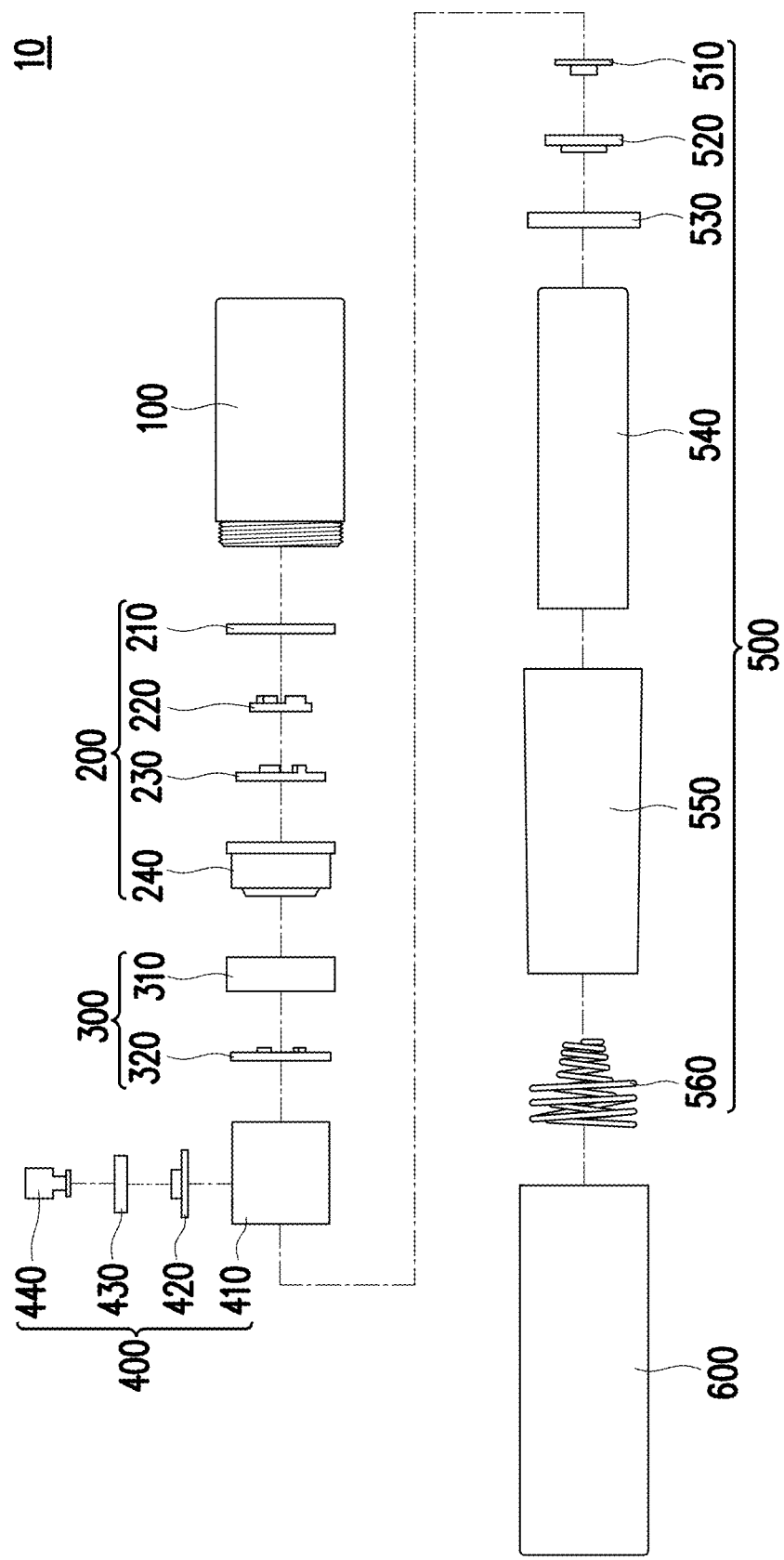
FIG. 2 is an exploded view of the LED therapeutic device.
Figure 3:
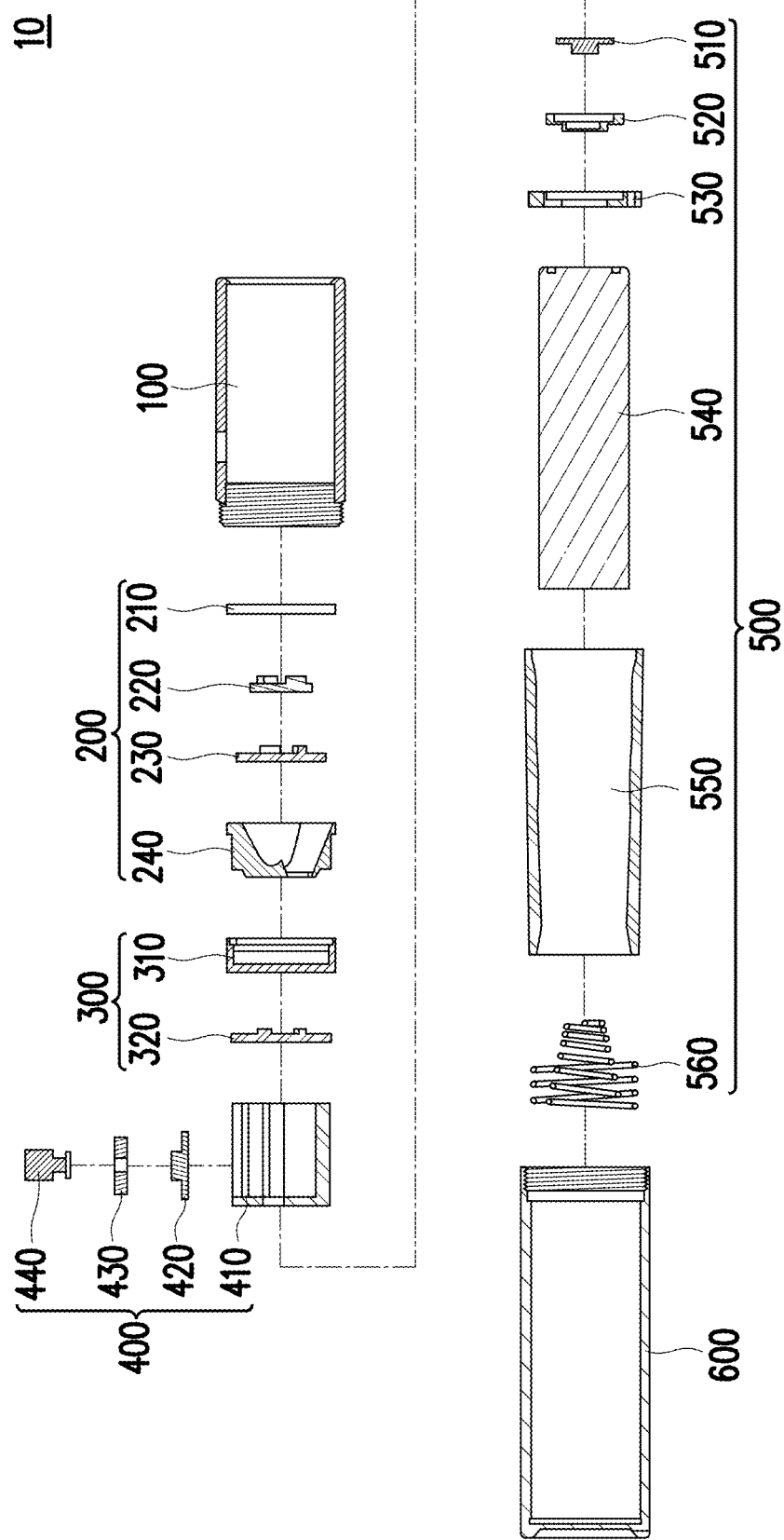
FIG. 3 is a cross-sectional and exploded view of the LED therapeutic device.
Figure 4:
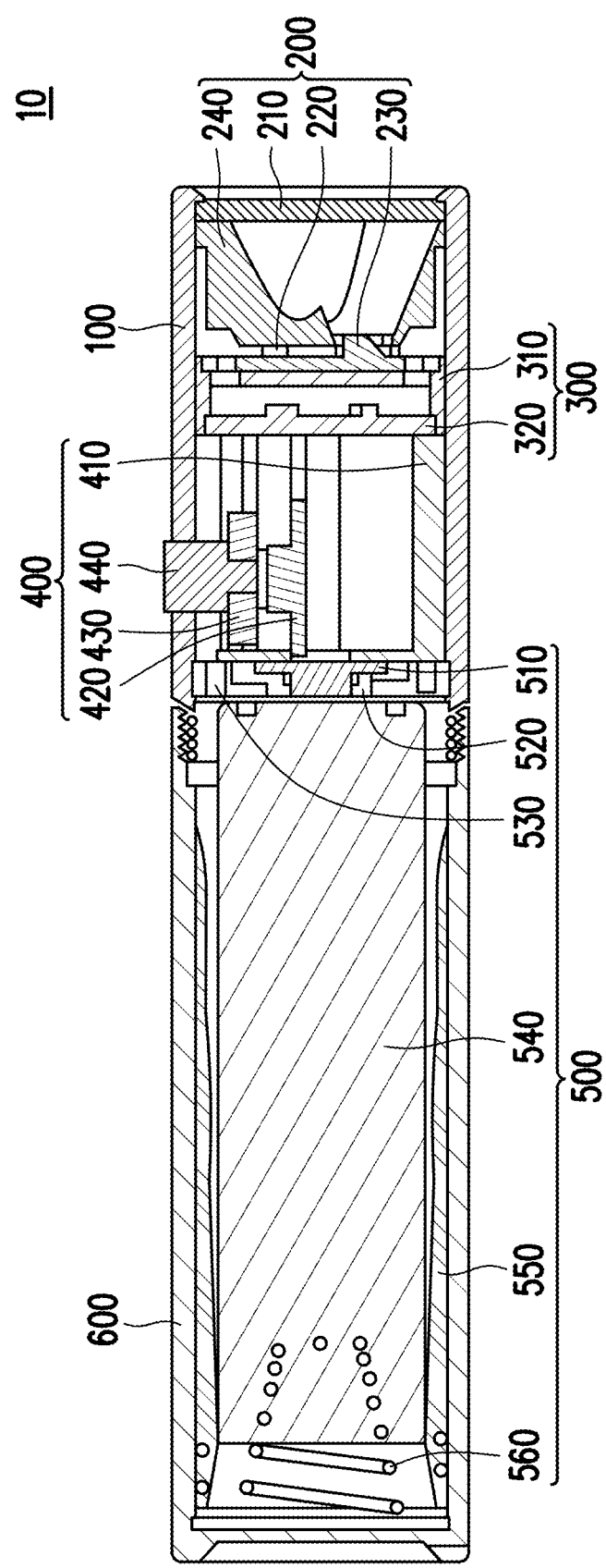
FIG. 4 is a cross-sectional view of the LED therapeutic device.

FIG. 1 is a perspective view of a LED therapeutic device 10. FIG. 2 is an exploded view of the LED therapeutic device 10. FIG. 3 is a cross-sectional and exploded view of the LED therapeutic device 10. FIG. 4 is a cross-sectional view of the LED therapeutic device 10.

Referring to FIGS. 1-4, the LED therapeutic device 10 of the present application comprises a top case 100, a light assembly 200, a controller 300, a switch assembly 400, a you supply 500 and a bottom case 600.

The top case 100 comprises aluminum. More specifically, the top case 100 is made of adonized aluminum. The weight for aluminum case is lighter than stainless steel as shown in current market. In addition, aluminum dissipates heat up to 15 times faster than stainless steel, keeping other components cool. It is ideal for electronic device for better thermal management to improve reliability and safer and more comfortable to use for treatment. In the present application, the top case 100 is cylindrical as an example but is not limited as long as the light assembly 200, the controller 300 and the switch assembly 400 may be located therein.

The light assembly 200 comprises a lens 210, an insulator 220, a LED assembly 230 and a reflector 240. The lens 210 is coupled to one end of the top case 100 as a clear window for light transmission. The insulator 210 is coupled between the reflector 240 and the LED assembly 230. The insulator also works as a retainer pad to secure the LED assembly 230. The LED assembly 230 of the present application comprises at least one visible light LED and at least one infrared LED. More details about the LED assembly 230 will be described later with FIGS. 5A-5B. The reflector 240 is coupled between the lens 210 and the LED assembly 230 for maximize the light output. The external and internal shapes of the reflector 240 are not limited in the present application as long as the reflector 240 could increase the light output.

The controller 300 comprises a circuit control block 310 and a circuit control panel 320. The circuit control panel 320 is surrounded by the circuit control block 310. The circuit control panel 320 of the controller 300 is electrically coupled to the light assembly 200 to control the light.

The switch assembly 400 is located inside the top case 100 in the present application but is not limited thereto as long as the user could turn on/off the LED therapeutic device 10 by the switch assembly 400. The switch assembly 400 comprises a positioning retainer block 410, a switch board 420, a switch retainer 430 and a button 440. The positioning retainer block 410 secures the other components of the switch assembly 400. Specifically, the switch board 420, the switch retainer 430 and part of the button 440 are surrounded by the positioning retainer block 410. The switch board 420 is electrically coupled to the controller 300. The switch retainer 430 is located between the button 440 and the switch board 420 to secure the connection between the button 440 and the switch board 420. The button 440 is coupled to the switch board 420. The button 400 is partially located inside the positioning retainer block 410 and partially protruded outside the top case 100. Specifically, as shown in FIG. 1, the top case 100 comprises a hole 110. Part of the button 400 is protruded outside the top case 100 via the hole 110, allowing the user to press the button 440 to turn on/off the LED therapeutic device 10. The shapes of the button 440 and the hole 110 are not limited in the present application as long as the user may turn on/off the LED therapeutic device 10 via the button 440.

The power supply 500 is electrically coupled to the controller 300. Specifically, the power supply 500 comprises a positive anode board 510, an anode insulation 520, an o-ring 530, a battery 540, a battery barrel 550 and a battery spring 560.

The positive anode board 510 is electrically coupled to the controller 300 via the switch assembly 400. The anode insulation pad is coupled to the positive anode 510. The positive anode board 510 and the anode insulation pad 520 are surrounded by the o-ring 530. The positive anode board 510, the anode insulation pad 520 and the o-ring 530 are located inside the top case 100 in the present application as an example but are not limited.

The battery 540 is a rechargeable battery. More specifically, the battery 540 is a high capacity lithium rechargeable battery. FIGS. 6A-6B show general information and the test result of the battery 540.

However, the battery 540 of LED therapeutic device 10 of the present application is not limited in the above battery. The power supply 500 may also be another kind of power supply such as USB charging or plug-in style as long as the power supply 500 could provide power to the LED therapeutic device 10.

The battery 540 is surrounded by the battery barrel 550. Specifically, the battery barrel 550 is fixed with inner side wall of the bottom case 600 to provide a suitable accommodation size for the battery 540 to prevent battery 540 from moving. The battery spring 560 is fixed with inner bottom of the bottom case 600. The battery 540 is electrically coupled between the battery spring 560 and the positive anode board 510 to assure better current conduction.

The bottom case 600 comprises aluminum. More specifically, the bottom case 600 is made of adonized aluminum. As mentioned above, the weight for aluminum case is lighter than stainless steel as shown in current market. In addition, aluminum dissipates heat up to 15 times faster than stainless steel, keeping other components cool. In the present application, the bottom case 600 is cylindrical as an example but is not limited as long as the bottom case 600 could be removably coupled to the top case 100.

In the present application, the overall size of the LED therapeutic device 10 is 26 mm (width) with 120.5 mm (length) as an example but is not limited. By the above structure, as an example but is not limited, the net weight of the LED therapeutic device 100 without the battery 540 is around 4.4 oz (0.12 kg). However, if the above-structured LED therapeutic device 10 is modified to be made of stain steel, the net weight would be around 7.4 oz (0.21 kg). It is much lighter to the patient to hold for long time in order to get treatment. Also, aluminum material allows the LED therapeutic device 10 to dissipate heat quickly and effectively. The LED therapeutic device 10 may remain cool during the entire treatment period which leads to an overall better user-experience.

The aluminum material avoids the common problem of overheating, thereby making it more effective and convenient to use than current therapeutic devices. The LED therapeutic device 10 may remain cool in the hand while the user is using and holding it during self-care procedures from home. The portability of the LED therapeutic device 10 also ensures that it also can be used for treating acute pain outside of the home, for traveling and on the go.

In addition, the size of the LED therapeutic device 10 is also suitable for treating and accessing tight spaces and deeper areas such as within the nose and mouth, making it be convenient for intra-oral and intranasal application.

Figure 5A:
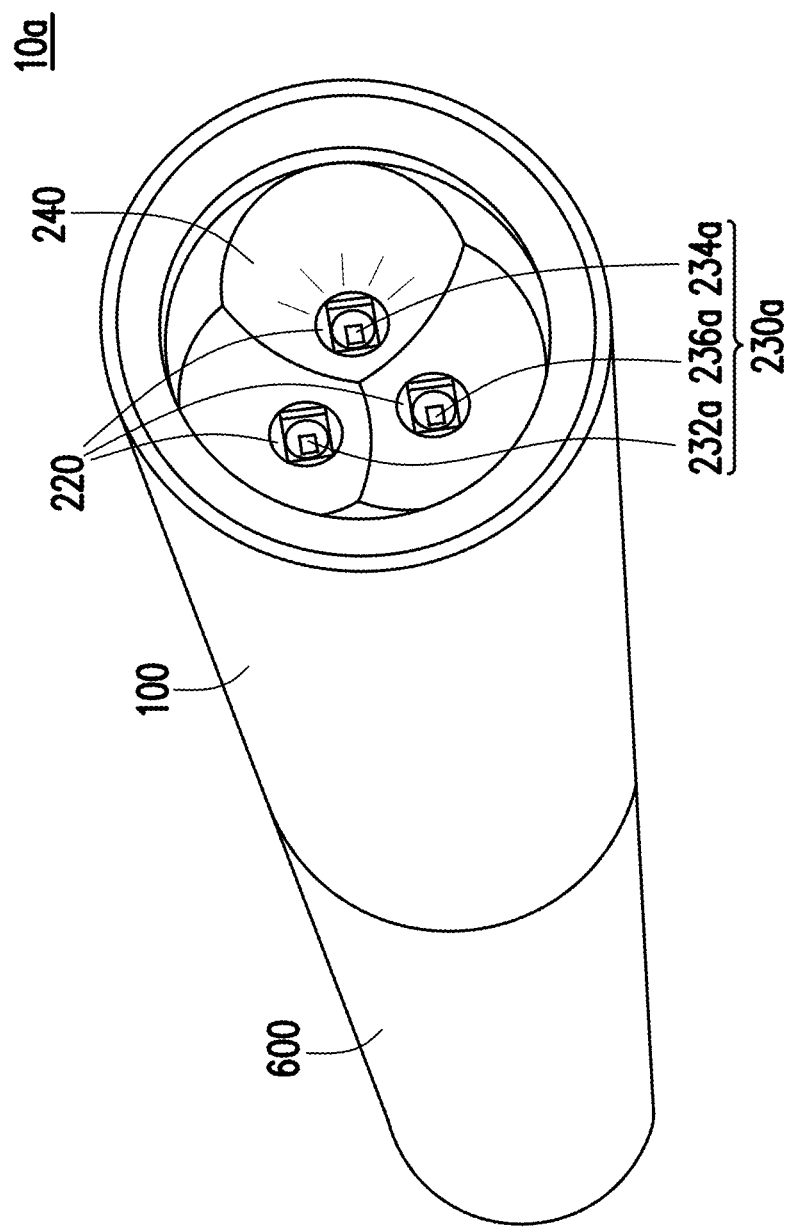
FIG. 5A is another perspective view showing one embodiment of the LED therapeutic device.

FIG. 5A is another perspective view showing one embodiment of the LED therapeutic device 10a.

As shown in FIG. 5A, the LED assembly 230a of the LED therapeutic device 10a of the present application comprises two infrared LEDs 232a/236a and one visible light LED 234a. Specifically, the wavelength of the infrared LED 232a is 850 nm and the wavelength of the infrared LED 236a is 940 nm. The visible light LED 234a is a red light and the wavelength is 660 nm. As such, as shown in FIG. 5A, only the visible light LED 234a is shining when turning on the LED therapeutic device 10a.

By the above deep penetrating wavelengths structure, the LED therapeutic device 10a may be effective in treatments such as for temporomandibular joint and oro-facial pain, swollen tissues, osteoarthritis, inflammation of the complex joints (such as shoulders, knees elbows, wrists and/or hands), neuropathy, carpal tunnel syndrome and/or sports injuries etc.

The combination of above wavelengths allows the light to penetrate safely and non-invasively into soft and deep tissue up to 40 mm. It makes the LED therapeutic device 10a a good treatment-modality for healing sore and fatigued muscles, joint-pain, bone and/or nerve damage such as oral application and beyond. Simply put, the treatment of the LED therapeutic device 10a not only reach skin and muscle but ligament, bone and nerve tissues etc.

Figure 5B:
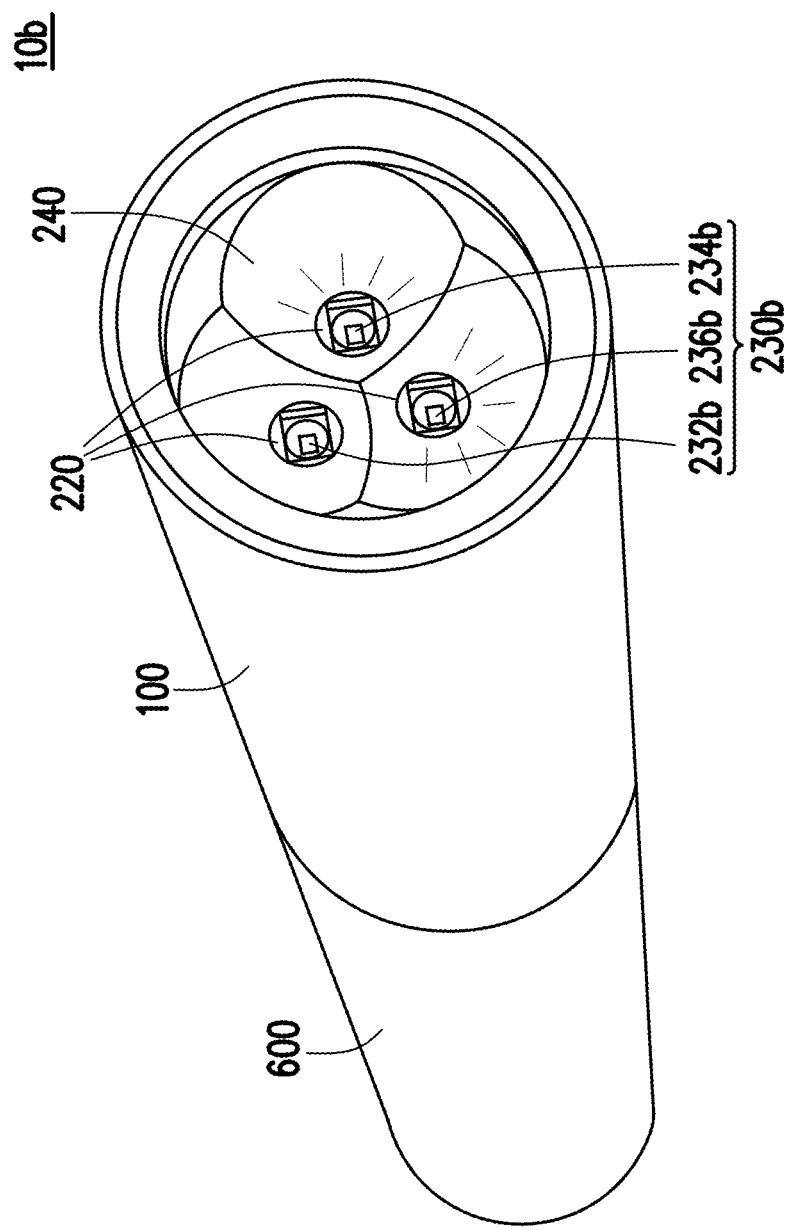
FIG. 5B is the other perspective view showing another embodiment of the LED therapeutic device.

FIG. 5B is the other perspective view showing another embodiment of the LED therapeutic device 10b.

As shown in FIG. 5B, the LED assembly 230b of the LED therapeutic device 10b of the present application comprises one infrared LED 232b and two visible light LEDs 234b/236b. Specifically, the wavelength of the infrared LED 232b is 850 nm. The visible light LED 234b is a red light and the wavelength is 630 nm. The visible light LED 236b is a red light and the wavelength is 660 nm. As such, as shown in FIG. 5B, the visible light LEDs 234b/236b are shining when turning on the LED therapeutic device 10b.

By the above deep penetrating wavelengths structure, the LED therapeutic device 10b may be effective in treatments such as for temporomandibular joint and oro-facial pain, surface wounds, sore muscle and sports injuries, swollen tissues, mouth sores (such as oral mucositis), post-op discomfort and promote healing and/or inflamed joints etc.

The irradiance for both the LED therapeutic device 10a and the LED therapeutic device 10b is around 120 mW/cm$^2$ when contacting skin and around 40 mW/cm$^2$ when keeping 1" distance from skin.

The fluence after five minutes for both the LED therapeutic device 10a and the LED therapeutic device 10b is 11.5 J/cm$^2$ when contacting skin and around 3.8 J/cm$^2$ when keeping 1" distance from skin.

Based on the above, the LED therapeutic device of the present application provide a portable device with lighter weight by utilize the aluminum as a main material for the top case and the bottom case. As such, patient may use the LED therapeutic device of the present application anywhere they want and on a daily basis.

In addition, the combination of visible light and infrared light may also provide a more therapeutic treatment for the patient. Specifically, compared with other wavelengths, it is evidence-based for the combined-usage of the wavelengths mentioned in the present application to have more clinical efficacy.

It will be apparent to those skilled in the art that various modifications and variations can be made to the structure of the present application without departing from the scope or spirit of the present application. In view of the foregoing, it is intended that the present application cover modifications and variations of this application provided they fall within the scope of the following claims and their equivalents.

What is claimed is:

1. A portable light emitting diode (LED) therapeutic device, comprising:
   a top case having a first end and a second end opposite to the first end;
   a light assembly embedded in an interior space of the top case and comprising:
      a lens coupled to the first end of the top case;
      a LED assembly close to the lens and comprising three LEDs, configured to emit visible light with a wavelength of 660 nm and infrared light with a wavelength of 850 nm; and
      a reflector assembly coupled to the LED assembly and comprising three segments laterally connected to one another and oriented toward the lens, with each of the LEDs disposed in an opening within one of the three segments;
   a controller electrically coupled to the light assembly and configured to control the light assembly to emit an irradiance of 100-140 mW/cm$^2$ when the portable LED therapeutic device is in contact with skin;
   a switch assembly coupled to the controller;
   a bottom case removably coupled to the second end of the top case; and
   a power supply electrically coupled to the controller and embedded in an interior space of the bottom case.

2. The portable LED therapeutic device as claimed in claim 1, wherein the light assembly further comprises an insulator coupled between the reflector assembly and the LED assembly.

3. The portable LED therapeutic device as claimed in claim 1, wherein top case comprises aluminum.

4. The portable LED therapeutic device as claimed in claim 3, wherein the top case is made of aluminum.

5. The portable LED therapeutic device as claimed in claim 1, wherein the bottom case comprises aluminum.

6. The portable LED therapeutic device as claimed in claim 5, wherein the bottom case is made of aluminum.

7. The portable LED therapeutic device as claimed in claim 1, wherein the controller comprises:
   a circuit control block; and
   a circuit control panel surrounded by the circuit control block.

8. The portable LED therapeutic device as claimed in claim 1, wherein the switch assembly is located inside the top case.

9. The portable LED therapeutic device as claimed in claim 1, wherein the switch assembly comprises:
   a switch board coupled to the controller;
   a button coupled to the switch board; and
   a switch retainer located between the button and the switch board.

10. The portable LED therapeutic device as claimed in claim 9, wherein the switch assembly further comprises a positioning retainer block, wherein the switch board and the switch retainer are surrounded by the positioning retainer block.

11. The portable LED therapeutic device as claimed in claim 1, wherein the power supply comprises:
   a positive anode board electrically coupled to the controller via the switch assembly;
   an anode insulation pad coupled to the positive anode;
   an o-ring, wherein the positive anode board and the anode insulation pad are surrounded by the o-ring;

a battery spring;

a battery coupled between the battery spring and the positive anode board; and a battery barrel, wherein the battery is surrounded by the battery barrel.

12. The portable LED therapeutic device as claimed in claim 1, wherein the power supply comprises a singular lithium battery.

* * * * *